(12) United States Patent
Murakami et al.

(10) Patent No.: US 10,525,443 B2
(45) Date of Patent: Jan. 7, 2020

(54) WATER-ABSORBENT RESIN AND ABSORBENT ARTICLE

(71) Applicant: Sumitomo Seika Chemicals Co. Ltd., Kako-gun (JP)

(72) Inventors: Masahiro Murakami, Himeji (JP); Tetsuhiro Hinayama, Himeji (JP); Hiroki Yabuguchi, Himeji (JP); Hideki Yokoyama, Himeji (JP)

(73) Assignee: Sumitomo Seika Chemicals Co. Ltd., Kako-gun (JP)

( * ) Notice: Subject to any disclaimer, the term of this patent is extended or adjusted under 35 U.S.C. 154(b) by 329 days.

(21) Appl. No.: 15/324,778

(22) PCT Filed: Nov. 4, 2014

(86) PCT No.: PCT/JP2014/079245
§ 371 (c)(1),
(2) Date: Jan. 9, 2017

(87) PCT Pub. No.: WO2016/006132
PCT Pub. Date: Jan. 14, 2016

(65) Prior Publication Data
US 2017/0203279 A1    Jul. 20, 2017

(30) Foreign Application Priority Data

Jul. 11, 2014  (JP) ................................ 2014-143717
Oct. 31, 2014  (JP) ................................ 2014-223724

(51) Int. Cl.
| | | |
|---|---|---|
| B01J 20/26 | (2006.01) | |
| C08F 220/06 | (2006.01) | |
| C08F 20/06 | (2006.01) | |
| A61L 15/24 | (2006.01) | |
| C08J 3/24 | (2006.01) | |

(52) U.S. Cl.
CPC ............. B01J 20/267 (2013.01); A61L 15/24 (2013.01); C08F 20/06 (2013.01); C08F 220/06 (2013.01); C08J 3/245 (2013.01)

(58) Field of Classification Search
CPC ......... B01J 20/267; A61L 15/24; C08F 20/06; C08F 220/06; C08J 3/245
See application file for complete search history.

(56) References Cited

U.S. PATENT DOCUMENTS

| | | | |
|---|---|---|---|
| 5,562,646 A | 10/1996 | Goldman et al. | |
| 5,760,080 A | 6/1998 | Wada et al. | |
| 6,565,768 B1 | 5/2003 | Dentler et al. | |
| 6,951,911 B2 | 10/2005 | Tagawa et al. | |
| 2002/0128618 A1* | 9/2002 | Frenz ...................... | A61L 15/60 604/368 |
| 2003/0078349 A1* | 4/2003 | Tagawa ............. | A61F 13/15203 526/89 |
| 2007/0093766 A1 | 4/2007 | Yoshino et al. | |
| 2008/0280154 A1 | 11/2008 | Kobushi et al. | |
| 2014/0031203 A1 | 1/2014 | Kondo et al. | |
| 2015/0216740 A1 | 8/2015 | Watanabe et al. | |

FOREIGN PATENT DOCUMENTS

| | | |
|---|---|---|
| CN | 1441813 A | 9/2003 |
| EP | 2893974 A1 | 7/2015 |
| EP | 2993190 A1 | 3/2016 |
| EP | 3153528 A1 | 4/2017 |
| JP | 61-271303 A | 12/1986 |
| JP | 64-038406 A | 2/1989 |
| JP | 08-057311 A | 3/1996 |
| JP | 09-510889 A | 11/1997 |
| JP | 11-335404 A | 12/1999 |
| JP | 2002-527547 A | 8/2002 |
| JP | 2003-088551 A | 3/2003 |
| JP | 2003-088552 A | 3/2003 |
| JP | 2005-111474 A | 3/2005 |
| JP | 2006-176570 A | 7/2006 |
| JP | 2008-133396 A | 6/2008 |

(Continued)

OTHER PUBLICATIONS

Office Action dated Nov. 1, 2018, issued in the SG Patent Application No. SG11201700205S.
International Search Report dated Dec. 16, 2014, issued for PCT/JP2014/079245.
Extended European Search Report dated Nov. 24, 2017, issued to EP Patent Application No. 14897110.4.
Notification that the Japan Patent Office received an Information Statement by a third party issued in JP Patent Application 2015-122358 dated Jul. 30, 2019 (in Japanese language).
Notification of Reasons for Refusal issued in the JP Patent Application No. 2015-122358 dated Sep. 3, 2019 (in Japanese language).

(Continued)

*Primary Examiner* — Roberto Rabago
(74) *Attorney, Agent, or Firm* — Locke Lord LLP

(57) ABSTRACT

Provided is: a water-absorbent resin which has a better water absorption performance and with which it is possible to improve absorption performance under a load when used in an absorbent material. This water-absorbent resin, obtained by polymerising a water soluble ethylenically unsaturated monomer in the presence of an internal-crosslinking agent and by post-crosslinking using a post-crosslinking agent, has a water-absorption capacity of physiological saline under a load of 4.14 kPa of 16 mL/g or more, has a mass proportion of particles from 150 to 850 μm relative to the whole proportion of 85 mass % or more, moreover has a mass proportion of particles from 300 to 400 μm relative to the whole proportion of 20 mass % or more, and has an absorption capacity elasticity index represented by formula (I) of 68,000 or more. Absorption capacity elasticity index=storage elastic modulus [Pa]×centrifugal retention rate [g/g] . . . (I).

5 Claims, 1 Drawing Sheet

(56) References Cited

FOREIGN PATENT DOCUMENTS

| | | | |
|---|---|---|---|
| JP | 2011-045724 | A | 3/2011 |
| JP | 2012-236898 | A | 12/2012 |
| JP | 2012236898 | A † | 12/2012 |
| WO | 2005/027986 | A1 | 3/2005 |
| WO | 2006/123561 | A1 | 11/2006 |
| WO | 2012/144564 | A1 | 10/2012 |
| WO | 2014/038324 | A1 | 3/2014 |
| WO | 2014/110328 | A1 | 7/2014 |

OTHER PUBLICATIONS

Written Opinion submitted by Applicant for JP Application No. 2014-534248 dated Aug. 1, 2017 (in English language and Japanese language), first cited in JP Patent Application 2015-122358 dated Jul. 30, 2019.

\* cited by examiner
† cited by third party

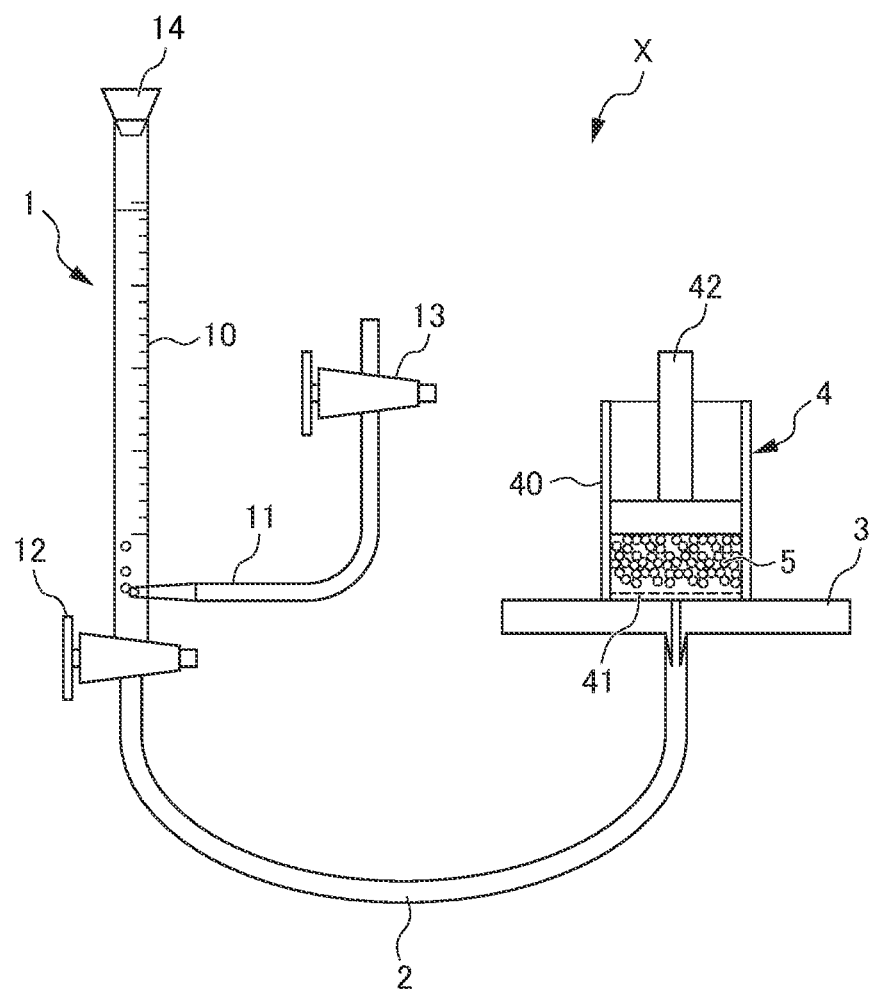

WATER-ABSORBENT RESIN AND ABSORBENT ARTICLE

TECHNICAL FIELD

The present invention relates to a water-absorbent resin and an absorbent article, and more particularly relates to a water-absorbent resin forming an absorbent material suitably used for hygienic materials such as disposable diapers, sanitary napkins and incontinence pads and to an absorbent article using it.

BACKGROUND ART

In recent years, water-absorbent resins have been widely used in the fields of hygienic materials such as disposable diapers, sanitary napkins and incontinence pads.

For water-absorbent resins as described above, cross-linked products of partially neutralized polymers of acrylic acid are preferred because they have many advantages, including the followings: they have better water-absorption performance; their raw materials such as acrylic acid has easy industrial availability, and therefore they can be produced with stable quality and low cost; and they show no shortcomings such as in which decomposition and degradation are likely to occur.

On the other hand, an absorbent article such as a disposable diaper, a sanitary napkin or an incontinence pad is formed with: an absorbent material which is mainly arranged in a center portion and which absorbs and holds body fluids such as urine and menstrual blood that are excreted from the body; a front surface sheet (top sheet) which is arranged on a side in contact with the body and which is liquid permeable; and a back surface sheet (back sheet) which is arranged on a side opposite to the side in contact with the body and which is not is liquid permeable. The absorbent material is formed with a hydrophilic fiber such as pulp and a water-absorbent resin.

In recent years, in terms of the design, the convenience at the time of carrying, the efficiency at the time of distribution and the like, it has been more required to reduce the thickness and the weight of the absorbent article. Furthermore, in terms of environmental protection, there are growing needs on a so-called eco-friendly orientation in which resources are effectively utilized to minimizing the usage of natural materials such as trees that it takes a long period of time to grow. Conventionally, as a method for reducing the thickness of the absorbent article which is generally performed, for example, there is a method of reducing a hydrophilic fiber such as the crushed pulp of wood, which serves to fix a water-absorbent resin in an absorbent material, and of increasing the water-absorbent resin.

The absorbent material in which the ratio of the hydrophilic fiber is lowered and in which a large amount of water-absorbent resin is used is preferable for reducing the thickness in terms of reducing the bulky hydrophilic fiber and holding a liquid. However, for example, in a case that a load is applied by deformation, pressure or the like to the absorbent material containing the water-absorbent resin, for example, when an infant wearing an absorbent article whose thickness is reduced sits, the re-wet (liquid back) of a to-be-absorbed liquid may not be able to be fully prevented. Furthermore, in the case of such an absorbent article, the absorbent article cannot stand urination which is performed a plurality of times, and thus a user may have an uncomfortable feeling.

A large amount of water-absorbent resin is formed into the shape of a soft gel by the absorption of the liquid, and furthermore, when a load is applied to the gel, a so-called "gel blocking phenomenon" occurs, and thus the liquid diffusibility is significantly lowered, with the result that the permeation rate of the liquid by the absorbent material may be lowered. The "gel blocking phenomenon" refers to a phenomenon in which especially when the absorbent material where a large amount of water-absorbent resin is densely present absorbs the liquid, the water-absorbent resin present around a front layer absorbs the liquid to form a soft gel around the front layer and the gel becomes dense to prevent the permeation of the liquid into the absorbent material, with the result that the water-absorbent resin therewithin cannot efficiently absorb the liquid.

Hence, as a means for preventing the problem occurring when the hydrophilic fiber is reduced and a large amount of water-absorbent resin is used, for example, the following methods have so far been proposed: a method (see Patent Document 1) of using a hydrogel water-absorbent polymer having specific saline flow conductivity, performance under pressure and the like; and a method (see Patent Document 2) of using a water-absorbent resin obtained by heating and processing a specific surface crosslinking agent on a specific water-absorbent resin precursor.

In these methods, however, the absorption performance of the absorbent material where a large amount of water-absorbent resin is used is not always satisfied, and there is a tendency that a to-be-absorbed liquid cannot be captured, and that thus the liquid disadvantageously leaks.

PRIOR ART DOCUMENT

Patent Documents

Patent Document 1: Japanese Unexamined Patent Application (Translation of PCT Application), Publication No. H9-510889

Patent Document 2: Japanese Unexamined Patent Application, Publication No. H8-57311

DISCLOSURE OF THE INVENTION

Problems to be Solved by the Invention

The present invention is proposed in view of the foregoing situations, and has an object to provide a water-absorbent resin in which the absorption performance is better and in which, when the water-absorbent resin is used as an absorbent material, it is possible to enhance the absorption performance under a load, and an object to provide an absorbent article which uses the absorbent material containing the water-absorbent resin.

Means for Solving the Problems

The present inventors have performed thorough studies to solve the problems described above. Consequently, they have found that a water-absorbent resin whose absorption capacity elasticity index indicated by the product of the storage elastic modulus and the centrifuge retention rate of the water-absorbent resin is equal to or more than a predetermined value is used as an absorbent article, and thus better absorption performance under a load is achieved. Specifically, the present invention provides the followings.

(1) The present invention provides a water-absorbent resin which is obtained by polymerizing a water-soluble ethylenically unsaturated monomer in the presence of an internal-crosslinking agent and performing post-crosslinking with a post-crosslinking agent, where a water-absorption capacity of physiological saline under a load of 4.14 kPa is 16 mL/g or more, a mass proportion of particles from 150 to 850 μm relative to the whole proportion is 85 mass % or more, moreover a mass proportion of particles from 300 to 400 μm relative to the whole proportion is 20 mass % or more, and an absorption capacity elasticity index represented by formula (I) is 68000 or more.

absorption capacity elasticity index=storage elastic
    modulus [Pa]×centrifugal retention rate [g/g]          (I)

(2) The present invention provides, in the invention according to above (1), the water-absorbent resin, where tan δ measured by sizing the 300 to 400 μm particles of the water-absorbent resin is $2.00 \times 10^{-2}$ or less.

(3) The present invention provides an absorbent article which is formed with an absorbent material containing the water-absorbent resin according to above (1) or (2).

Effects of the Invention

The water-absorbent resin of the present invention has better absorption performance under a load and can form a gel which has appropriate elasticity at the time of absorption of a liquid. Hence, an absorbent article using an absorbent material containing the water-absorbent resin can effectively reduce the re-wet of a to-be-absorbed liquid over time even in a state where a load is applied by deformation, pressure or the like, and can achieve better absorption performance under a load.

BRIEF DESCRIPTION OF THE DRAWINGS

FIG. 1 is a pattern diagram showing the schematic arrangement of an apparatus for measuring, in a water-absorbent resin, a water-absorption capacity of physiological saline under a load of 4.14 kPa.

PREFERRED MODE FOR CARRYING OUT THE INVENTION

The present invention will be described in detail below.

1. Water-Absorbent Resin

A water-absorbent resin according to the present invention has the following properties.

In a water-absorbent resin according to the present invention, a water-absorption capacity of physiological saline under a load of 4.14 kPa is 16 mL/g or more, a mass proportion of particles from 150 to 850 μm relative to the whole proportion is 85 mass % or more, moreover a mass proportion of particles from 300 to 400 μm relative to the whole proportion is 20 mass % or more, and an absorption capacity elasticity index represented by formula (I) is 68000 or more.

absorption capacity elasticity index=storage elastic
    modulus [Pa]×centrifugal retention rate [g/g]          (I)

In the particle size distribution of the water-absorbent resin, the mass proportion of particles from 150 to 850 μm relative to the whole proportion is preferably 85 mass % or more, and more preferably 90 mass % or more. Furthermore, the mass proportion of particles from 300 to 400 μm relative to the whole proportion is preferably 20 mass % or more, more preferably 25 mass % or more and further preferably 30 mass % or more.

The particles of the water-absorbent resin may be in the form in which each particle is formed with a single particle or may be in the agglomerated form (secondary particles) by fine particles (primary particles). Examples of the shape of the primary particles include a substantially spherical shape, an irregularly fractured shape and a plate shape. In the case of primary particles produced by reverse phase suspension polymerization, as an example, a substantially spherical single-particle shape having a smooth surface shape such as a spherical shape or an oval spherical shape is taken up. Since the surface shape is smooth in the primary particles with such a shape to increase the flowability of the powder thereof, and the agglomerated particles are easily and densely packed, there is a tendency that the secondary particles are unlikely to be broken by a shock, and that the water-absorbent resin having a high particle strength is obtained.

The median particle diameter of the water-absorbent resin according to the present invention is preferably 200 to 600 μm, is more preferably 250 to 500 μm and is further preferably 300 to 400 μm.

In the water-absorbent resin according to the present invention, as described above, the absorption capacity elasticity index represented by formula (I) described above is 68000 or more. It is found that as the water-absorbent resin has a higher index described above, the absorption performance (such as the permeation rate and the amount of re-wet) under a load in an absorbent article using it is far better. The absorption capacity elasticity index is preferably 70000 or more, is more preferably 72000 or more and is further preferably 74000 or more. Moreover, the absorption capacity elasticity index is preferably 200000 or less, is more preferably 150000 or less and is further preferably 100000 or less.

The "storage elastic modulus" here refers to a value obtained by measuring, with a dynamic viscoelasticity measuring device, a swollen gel produced by swelling, with physiological saline, the sized sample of 300 to 400 μm in the water-absorbent resin to fifty times. The storage elastic modulus is an index indicating a ratio of the strain to the stress of the gel, that is, the shape-retaining property (deformation resistance) of the gel.

The "centrifuge retention rate" refers to a parameter indicating that the water-absorbent resin sample is swollen (absorbed) with physiological saline for 60 minutes under stirring and is further dehydrated with a centrifugal force of 167 G for one minute and that thereafter how many times the swelling ratio of its weight can be held by the water-absorbent resin.

In the water-absorbent resin according to the present invention, the absorption capacity elasticity index represented by formula (I) described above is 68000 or more, and in the water-absorbent resin having such a property, a gel having appropriate elasticity is formed while a high centrifuge retention rate is being held, and thus it is possible to effectively reduce the re-wet of a to-be-absorbed liquid over time by deformation, pressure or the like in an absorbent material using it. For example, when this water-absorbent resin is used to form an absorbent article such as a disposable diaper, it is significantly advantageous over urination which is performed a plurality of times and the uncomfortable feeling of a user is reduced, and thus it is possible to use it more comfortably. Further, it is possible to reduce the gel blocking phenomenon, with the result that it is also possible to enhance the absorption performance of the absorbent article under a load.

Furthermore, in the water-absorbent resin according to the present invention, the water-absorption capacity of physiological saline under a load of 4.14 kPa is 16 mL/g or more. The water-absorption capacity of physiological saline under a load of 4.14 kPa is preferably 18 mL/g or more, and is more preferably 20 mL/g or more. The water-absorption capacity of physiological saline under a load of 4.14 kPa is preferably 50 mL/g or less, and is more preferably 40 mL/g or less.

In the water-absorbent resin according to the present invention, as described above, tan δ measured by sizing the 300 to 400 μm particles is preferably $2.00 \times 10^{-2}$ or less. Here, the details of tan δ are described in, for example, "Viscoelasticity of Polymers" (written by John D. Ferry, translated by Hiroshi Sobue together with Jokichi Murakami and Masao Takahashi, published in October 1964 by Tokyo Kagaku Dojin).

In general, in viscoelasticity evaluation, a polymeric material is represented by a model consisting of an elastic component and a viscous component, the elastic component is a component which converts impact energy into repulsive energy and the viscous component is a component which converts impact energy into dissipated energy. In the measurement of dynamic viscoelasticity by vibration strain, complex elastic modulus $G^* = G' + iG''$ (i is an imaginary unit) is physically indicated. Here, G' (storage elastic modulus) and G'' (loss elastic modulus) respectively represent the magnitudes of the elastic component and the viscous component in the polymeric material. Then, tan δ (loss coefficient)=G''/G' is an index for energy lost when the material is deformed.

In the water-absorbent resin according to the present invention, that tan δ represented by "tan δ=loss elastic modulus/storage elastic modulus" is preferably $2.00 \times 10^{-2}$ or less means that a high storage elastic modulus is indicated, and it is also possible to reduce the gel blocking phenomenon occurring when a liquid is absorbed. Here, tan δ is more preferably $1.00 \times 10^{-2}$ or more.

In the water-absorbent resin according to the present invention, the storage elastic modulus is preferably 1000 Pa or more, is more preferably 1200 Pa or more and is further preferably 1500 Pa or more. The upper limit value of the storage elastic modulus is preferably 10000 Pa or less, is more preferably 5000 Pa or less, is further preferably 2500 Pa or less and is further more preferably 2000 Pa or less.

In the water-absorbent resin according to the present invention, the centrifuge retention rate is preferably 30 g/g or more. The centrifuge retention rate indicates the degree of the absorption capacity of a liquid in the water-absorbent resin. In the water-absorbent resin according to the present invention, the centrifuge retention rate is preferably 30 g/g or more, is more preferably 36 g/g or more, is further preferably 38 g/g or more and is further more preferably 40 g/g or more. The upper limit value of the centrifuge retention rate is preferably about 60 g/g or less, is more preferably 55 g/g or less and is further preferably 50 g/g or less.

In the water-absorbent resin described above, the centrifuge retention rate, the water-absorption capacity of physiological saline under a load of 4.14 kPa, the median particle diameter (particle size distribution), the storage elastic modulus and tan δ can be evaluated with evaluation tests described later in the examples respectively.

In order to provide various performances to the water-absorbent resin obtained, it is possible to combine additives corresponding to purposes to form a water-absorbent resin composition. Examples of such additives include an inorganic powder, a surfactant, an oxidizing agent, a reducing agent, a metal chelating agent, a radical chain inhibitor, an antioxidant, an antibacterial agent and a deodorant. For example, 0.05 to 5 mass parts of amorphous silica is added as an inorganic powder to 100 mass parts of the water-absorbent resin, and thus it is possible to enhance the flowability of the water-absorbent resin.

2. Method of Producing Water-Absorbent Resin

The water-absorbent resin according to the present invention can be produced by polymerizing a water-soluble ethylenically unsaturated monomer in the presence of an internal-crosslinking agent.

As the method of polymerizing the water-soluble ethylenically unsaturated monomer, a typical polymerization method such as an aqueous solution polymerization method, an emulsion polymerization method or a reverse phase suspension polymerization method is used. In the aqueous solution polymerization method, a water-soluble ethylenically unsaturated monomer aqueous solution is heated while being stirred as necessary, and thus the polymerization is performed. In the reverse phase suspension polymerization method, the water-soluble ethylenically unsaturated monomer is heated in a hydrocarbon dispersion medium under stirring, and thus the polymerization is performed. In the present invention, the reverse phase suspension polymerization method is preferable because it is possible to perform accurate polymerization reaction control and extensive particle diameter control.

An example of the method of producing the water-absorbent resin according to the present invention will be described below.

As a specific example of the method of producing the water-absorbent resin, in a method of producing the water-absorbent resin by performing the reverse phase suspension polymerization on the water-soluble ethylenically unsaturated monomer in a hydrocarbon dispersion medium that includes: a step of performing polymerization in the presence of an internal-crosslinking agent, at least in the presence of an azo based compound and a peroxide; and a step of performing, with a post-crosslinking agent, post-crosslinking on a hydrous gel-like material having an internal-crosslinking structure obtained by the polymerization.

<Polymerization Step>

[Water-Soluble Ethylenically Unsaturated Monomer]

Water-soluble ethylenically unsaturated monomers include, for example, (meth)acrylic acid ("(meth)acry" herein refers to both "acry" and "methacry". The same shall apply hereinafter) and salts thereof; 2-(meth)acrylamide-2-methylpropanesulfonic acid and salts thereof; nonionic monomers such as (meth)acrylamide, N,N-dimethyl(meth)acrylamide, 2-hydroxyethyl(meth)acrylate, N-methylol(meth)acrylamide, polyethylene glycol mono(meth)acrylate; amino group-containing unsaturated monomers such as N,N-diethylaminoethyl(meth)acrylate, N,N-diethylaminopropyl(meth)acrylate, diethylaminopropyl(meth)acrylamide and quaternary compounds thereof. Among these water-soluble ethylenically unsaturated monomers, (meth)acrylic acid or salts thereof, (meth)acrylamide, N,N-dimethylacrylamide are preferred in view of easy industrial availability, and (meth)acrylic acid and salts thereof are more preferred. Note that these water-soluble ethylenically unsaturated monomers may be used alone or in a combination of two or more.

Among these, acrylic acid and salts thereof are widely used as raw materials for water-absorbent resins, and may also be used in a case where the aforementioned water-soluble ethylenically unsaturated monomers are copolymerized with these partially neutralized acrylates. In this case, a partially neutralized acrylate is preferably used as a main water-soluble ethylenically unsaturated monomer in an amount of 70 to 100 mol % relative to the total amount of water-soluble ethylenically unsaturated monomers.

Preferably, a water-soluble ethylenically unsaturated monomer is dispersed in a hydrocarbon dispersion medium in the state of an aqueous solution, and subjected to reverse phase suspension polymerization. A water-soluble ethylenically unsaturated monomer in the form of an aqueous solution can increase the dispersion efficiency in a hydrocarbon dispersion medium. For the concentration of a water-soluble ethylenically unsaturated monomer in the aqueous solution, it is preferably in a range from 20 mass % to the saturation concentration or below. The concentration of the water-soluble ethylenically unsaturated monomer is more preferably 55 mass % or less, further preferably 50 mass % or less and further more preferably 45 mass % or less. On the other hand, the concentration of the water-soluble ethylenically unsaturated monomer is more preferably 25 mass % or more, and further preferably 28 mass % or more and further more preferably 30 mass % or more.

When a water-soluble ethylenically unsaturated monomer has an acid group such as (meth)acrylic acid, or 2-(meth)acrylamide-2-methylpropanesulfonic acid, those having the acid group pre-neutralized with an alkaline neutralizer may be used if desired. Such alkaline neutralizers include alkali metal salts such as sodium hydroxide, sodium carbonate, sodium hydrogen carbonate, potassium hydroxide, and potassium carbonate; and ammonia and the like. Further, these alkaline neutralizers may be used in the form of an aqueous solution in order to simply neutralization procedures. Note that the aforementioned alkaline neutralizers may be used alone or in a combination of two or more.

For the degree of neutralization of a water-soluble ethylenically unsaturated monomer with an alkaline neutralizer, the degree of neutralization of all acid groups in the water-soluble ethylenically unsaturated monomer is preferably 10 to 100 mol %, more preferably 30 to 90 mol %, further preferably 40 to 85 mol % and further more preferably 50 to 80 mol %.

[Internal-Crosslinking Agent]

Examples of the internal-crosslinking agent include internal-crosslinking agents that can crosslink the polymer of water-soluble ethylenically unsaturated monomers to be used. For example, unsaturated polyesters obtained by allowing polyols, for example, diols and triols such as (poly)ethylene glycol ("(poly)" means that the prefix "poly" is optional. The same shall apply hereinafter), (poly)propylene glycol, 1,4-butanediol, trimethylolpropane, (poly)glycerin to react with unsaturated acids such as (meth)acrylic acid, maleic acid, fumaric acid; bisacrylamides such as N,N-methylenebisacrylamide; di(meth)acrylic acid esters or tri(meth)acrylic acid esters obtained by allowing polyepoxide to react with (meth)acrylic acid; di(meth)acrylic acid carbamyl esters obtained by allowing polyisocyanate such as tolylene diisocyanate, hexamethylene diisocyanate to react with (meth)acrylic acid hydroxyethyl; compounds having two or more polymerizable unsaturated groups, for example, allylated starch, allylated cellulose, diallyl phthalate, N,N', N"-triallylisocyanate, divinylbenzene and the like; polyglycidyl compounds, for example, diglycidyl compounds such as (poly)ethylene glycol diglycidyl ether, (poly)propylene glycol diglycidyl ether, (poly)glycerin diglycidyl ether, triglycidyl compounds and the like; epihalohydrin compounds such as epichlorohydrin, epibromhydrin, and α-methyl epichlorohydrin; compounds having two or more reactive functional groups, for example, isocyanate compounds such as 2,4-tolylene diisocyanate, and hexamethylene diisocyanate; oxetane compounds such as 3-methyl-3-oxetane methanol, 3-ethyl-3-oxetane methanol, 3-butyl-3-oxetane methanol, 3-methyl-3-oxetane ethanol, 3-ethyl-3-oxetane ethanol, 3-butyl-3-oxetane ethanol. Among these internal-crosslinking agents, polyglycidyl compounds are preferably used, and diglycidyl ether compounds such as (poly)ethylene glycol diglycidyl ether, (poly)propylene glycol diglycidyl ether, (poly)glycerin diglycidyl ether are further preferably used. These internal-crosslinking agents may be used alone or in a combination of two or more.

For the used amount of the internal-crosslinking agent, it is preferably 0.000001 to 0.02 mol relative to 1 mol of a water-soluble ethylenically unsaturated monomer, more preferably 0.00001 to 0.01 mol, further preferably 0.00001 to 0.005 mol and further more preferably 0.00005 to 0.002 mol.

[Hydrocarbon Dispersion Media]

Hydrocarbon dispersion media include, for example, aliphatic hydrocarbons having 6 to 8 carbon atoms such as n-hexane, n-heptane, 2-methylhexane, 3-methylhexane, 2,3-dimethylpentane, 3-ethylpentane, and n-octane; alicyclic hydrocarbons such as cyclohexane, methylcyclohexane, cyclopentane, methylcyclopentane, trans-1,2-dimethylcyclopentane, cis-1,3-dimethylcyclopentane, and trans-1,3-dimethylcyclopentane; and aromatic hydrocarbons such as benzene, toluene, xylene and the like. Among these hydrocarbon dispersion media, in particular, n-hexane, n-heptane, and cyclohexane are suitably used in view of easy industrial availability, stable quality and low cost. These hydrocarbon dispersion media may be used alone or in a combination of two or more. Note that examples of a mixture of hydrocarbon dispersion media include commercially available products such as EXXSOL heptane (made by Exxon Mobil Corporation: containing 75 to 85 mass % of heptane and its isomeric hydrocarbons thereof), which can also produce a suitable result.

For the used amount of the hydrocarbon dispersion medium, it is preferably 100 to 1500 parts by mass relative to 100 parts by mass of a first-step water-soluble ethylenically unsaturated monomer, and more preferably 200 to 1400 parts by mass from the viewpoint that the water-soluble ethylenically unsaturated monomer can be uniformly dispersed to allow easy control over polymerization temperature. Note that as described below, reverse phase suspension polymerization is performed in one step (single step) or in multiple steps such as two or more steps, and the first-step polymerization described above means a polymerization reaction of single-step polymerization or of the first step in multiple-step polymerization (The same shall apply hereinafter).

[Dispersion Stabilizer]

(Surfactant)

In the reverse phase suspension polymerization, in order for dispersion stability in the hydrocarbon dispersion medium of the water-soluble ethylenically unsaturated monomer to be enhanced, a dispersion stabilizer can also be used. A surfactant can be used as the dispersion stabilizer.

As surfactants, the following may be used: for example, sucrose fatty acid ester, polyglycerin fatty acid ester, sorbitan fatty acid ester, polyoxyethylene sorbitan fatty acid ester, polyoxyethylene glycerine fatty acid ester, sorbitol fatty acid ester, polyoxyethylene sorbitol fatty acid ester, polyoxyethylene alkyl ether, polyoxyethylene alkyl phenyl ether, polyoxyethylene castor oil, polyoxyethylene hydrogenated castor oil, alkyl allyl formaldehyde condensed polyoxyethylene ether, polyoxyethylene polyoxypropylene block copolymer, polyoxyethylene polyoxy propyl alkyl ether, polyethylene glycol fatty acid ester, alkyl glucoside, N-alkyl gluconamide, polyoxyethylene fatty acid amide, polyoxyethylene alkylamine, phosphate ester of polyoxyethylene alkyl ether, phosphate ester of polyoxyethylene alkyl aryl ether and the like. Among these surfactants, in particular, sorbitan fatty acid ester, polyglycerin fatty acid ester, and sucrose fatty acid ester are preferably used in view of dispersion stability of monomers. These surfactants may be used alone or in a combination of two or more.

For the used amount of the surfactant, it is preferably 0.1 to 30 parts by mass relative to 100 parts by mass of a first-step water-soluble ethylenically unsaturated monomer, and more preferably 0.3 to 20 parts by mass.

(Polymeric Dispersion Agent)

A polymeric dispersion agent may also be used, along with a surfactant described above, as a dispersion stabilizer used in the reverse phase suspension polymerization.

Polymeric dispersion agents include, for example, maleic anhydride modified polyethylene, maleic anhydride modified polypropylene, maleic anhydride modified ethylene-propylene copolymer, maleic anhydride modified EPDM (ethylene-propylene-diene-terpolymer), maleic anhydride modified polybutadiene, maleic anhydride-ethylene copolymer, maleic anhydride-propylene copolymer, maleic anhydride-ethylene-propylene copolymer, maleic anhydride-butadiene copolymer, polyethylene, polypropylene, ethylene-propylene copolymer, oxidized polyethylene, oxidized polypropylene, oxidized ethylene-propylene copolymer, ethylene-acrylate copolymer, ethyl cellulose, ethyl hydroxyethyl cellulose and the like. Among these polymeric dispersion agents, particularly in view of dispersion stability of monomers, maleic anhydride modified polyethylene, maleic anhydride modified polypropylene, maleic anhydride modified ethylene-propylene copolymer, maleic anhydride-ethylene copolymer, maleic anhydride-propylene copolymer, maleic anhydride-ethylene-propylene copolymer, polyethylene, polypropylene, ethylene-propylene copolymer, oxidized polyethylene, oxidized polypropylene, and oxidized ethylene-propylene copolymer are preferably used. These polymeric dispersion agents may be used alone or in a combination of two or more.

For the used amount of the polymeric dispersion agents, it is preferably 0.1 to 30 parts by mass relative to 100 parts by mass of a first-step water-soluble ethylenically unsaturated monomer, and more preferably 0.3 to 20 parts by mass.

[Azo Based Compound and Peroxide]

In an example of the method of producing a water-absorbent resin, reverse phase suspension polymerization can be performed on the water-soluble ethylenically unsaturated monomer in the presence of an azo based compound and a peroxide.

Here, the phrase "in the presence of an azo based compound and a peroxide" does not necessarily means that the azo based compound and the peroxide are coexistent at the beginning of a polymerization reaction (at the time of the radical cleavage of a compound), but means that the other compound is present before a monomer conversion ratio by radical cleavage due to one compound becomes 10% or more. However, both are preferably coexistent in an aqueous solution containing a monomer before the start of the polymerization reaction. Further, an azo based compound and a peroxide may be added to a polymerization reaction system via different flow channels or may be sequentially added to the polymerization reaction system via the same flow channel.

Note that an azo based compound and a peroxide to be used may be in the form of powder or an aqueous solution.

(Azo Based Compound)

Specifically, Azo based compounds include, for example, those azo based compounds such as 1-{(1-cyano-1-methylethyl)azo}formamide, 2,2'-azobis[2-(N-phenyl amidino)propane]dihydrochloride, 2,2'-azobis{2-[N-(4-chlorophenyl)amidino]propane}dihydrochloride, 2,2'-azobis{2-[N-(4-hydroxyphenyl)amidino]propane}dihydrochloride, 2,2'-azobis[2-(N-benzyl amidino)propane]dihydrochloride, 2,2'-azobis[2-(N-allyl amidino)propane]dihydrochloride, 2,2'-azobis(2-amidinopropane)dihydrochloride, 2,2'-azobis{2-[N-(2-hydroxyethyl)amidino]propane}dihydrochloride, 2,2'-azobis[2-(5-methyl-2-imidazoline-2-yl)propane]dihydrochloride, 2,2'-azobis[2-(2-imidazoline-2-yl)propane]dihydrochloride, 2,2'-azobis[2-(4,5,6,7-tetrahydro-1H-1,3-diazepine-2-yl)propane]dihydrochloride, 2,2'-azobis[2-(5-hydroxy-3,4,5,6-tetrahydropyrimidine-2-yl)propane]dihydrochloride, 2,2'-azobis{2-[1-(2-hydroxyethyl)-2-imidazoline-2-yl]propane}dihydrochloride, 2,2'-azobis[2-(2-imidazoline-2-yl)propane], 2,2'-azobis{2-methyl-N-[1,1-bis(hydroxymethyl)-2-hydroxyethyl]propionamide}, 2,2'-azobis{2-methyl-N-[1,1-bis(hydroxymethyl)ethyl]propionamide}, 2,2'-azobis[2-methyl-N-(2-hydroxyethyl)propionamide], 2,2'-azobis(2-methylpropionamide)dihydrochloride, 4,4'-azobis-4-cyanovaleinic acid, 2,2'-azobis[2-(hydroxymethyl)propionitrile], 2,2'-azobis[2-(2-imidazoline-2-yl)propane]disulfate dihydrate, 2,2'-azobis[N-(2-carboxyethyl)-2-methylpropione amidine]tetrahydrate, 2,2'-azobis[2-methyl-N-(2-hydroxyethyl)propionamide]. Among these, 2,2'-azobis(2-amidinopropane)dihydrochloride, 2,2'-azobis{2-[1-(2-hydroxyethyl)-2-imidazoline-2-yl]propane}dihydrochloride, 2,2'-azobis[N-(2-carboxyethyl)-2-methylpropione amidine]tetrahydrate are particularly preferred because it is easy to adjust a polymerization reaction such as a polymerization temperature, and it is easy to obtain a water-absorbent resin having a high centrifuge retention rate and high water-absorption capacity under a load. These azo based compounds may be used alone or in a combination of two or more.

(Peroxide)

Peroxides include, for example, persulfates such as potassium persulfate, ammonium persulfate, and sodium persulfate; peroxides such as methyl ethyl ketone peroxide, methyl isobutyl ketone peroxide, di-t-butyl peroxide, t-butyl cumyl peroxide, t-butyl peroxyacetate, t-butyl peroxy isobutyrate, t-butyl peroxy pivalate, and hydrogen peroxide. Among these peroxides, since it is easy to obtain a water-absorbent resin having a storage elastic modulus, potassium persulfate, ammonium persulfate, sodium persulfate, and hydrogen peroxide are preferably used, and further, potassium persulfate, ammonium persulfate, and sodium persulfate are more preferably used. These peroxides may be used alone or in a combination of two or more.

(Used Amount and Used Proportion of Azo Based Compound and Peroxide)

For the used amount of an azo based compound and a peroxide, it is preferably 0.00005 mol or more relative to 1 mol of a water soluble ethylenically unsaturated monomer, more preferably 0.0001 mol or more. Further, the used amount is preferably 0.005 mol or less relative to 1 mol of a water-soluble ethylenically unsaturated monomer, and more preferably 0.001 mol or less.

For the used proportion of an azo based compound and a peroxide, the proportion of an azo based compound is preferably 40 mass % or more in the total used amount of an azo based compound and a peroxide, more preferably 50 mass % or more, further preferably 60 mass % or more and further more preferably 70 mass % or more. On the other hand, the proportion of an azo based compound is preferably 95 mass % or less in the total used amount of an azo based compound and a peroxide, more preferably 90 mass % or less, further preferably 85 mass % and further more preferably 80 mass % or less. The mass ratio range (azo based compound: peroxide) is preferably 8:12 to 19:1.

[Other Components]

In an example of the method of producing a water-absorbent resin, other components may be added to an aqueous solution containing a water-soluble ethylenically unsaturated monomer to perform reverse phase suspension polymerization if desired. As other components, various additives such as thickeners and chain transfer agents may be added.

(Thickener)

As an example, in a method of producing this water-absorbent resin, a thickener may be added to an aqueous solution containing a water-soluble ethylenically unsaturated monomer to perform polymerization. By adding a thickener to adjust the viscosity of an aqueous solution as described above, the median particle diameter obtained from polymerization can be controlled.

Specifically, as a thickener, for example, hydroxyethyl cellulose, hydroxypropyl cellulose, methyl cellulose, carboxymethyl cellulose, polyacrylic acid, (partially) neutralized polyacrylic acid, polyethylene glycol, polyacrylamide, polyethyleneimine, dextrin, sodium alginate, polyvinyl alcohol, polyvinyl pyrrolidone, polyethylene oxide and the like can be used. Note that in a case where the stirring speeds at the time of polymerization are the same, there is a tendency that the higher the viscosity of an aqueous solution of a water-soluble ethylenically unsaturated monomer, the larger the median particle diameter of the resulting particles.

[Reverse Phase Suspension Polymerization]

As an example of producing the water-absorbent resin, reverse phase suspension polymerization can be performed on the water-soluble ethylenically unsaturated monomer. When performing reverse phase suspension polymerization, for example, a water-soluble ethylenically unsaturated monomer is dispersed in a hydrocarbon dispersion medium in the presence of a surfactant and/or a polymeric dispersion agent. When doing this, a surfactant or a polymeric dispersion agent may be added either before or after the aqueous monomer solution is dispersed as long as they are added before starting a polymerization reaction.

In particular, in view of easy reduction of the amount of a residual hydrocarbon dispersion medium in the resulting water-absorbent resin, it is preferred that polymerization is performed after a water-soluble ethylenically unsaturated monomer is dispersed in a hydrocarbon dispersion medium in which a polymeric dispersion agent has been added and dispersed, and then a surfactant is further dispersed.

The reverse phase suspension polymerization can be performed as described above in a single step or multiple steps such as two or more steps. Further, in view of increasing productivity, it is preferably performed in 2 to 3 steps.

In a case where reverse phase suspension polymerization is performed in multiple steps such as two or more steps, after a first-step reverse phase suspension polymerization is performed, a water-soluble ethylenically unsaturated monomer may be added to the reaction mixture obtained in the first-step polymerization reaction, and mixed to perform a second-step reverse phase suspension polymerization as in the first step. Preferably, in a case of reverse phase suspension polymerization at each step of the second step and later steps, reverse phase suspension polymerization may be performed by adding, in addition to a water-soluble ethylenically unsaturated monomer, and an internal-crosslinking agent, an azo compound and a peroxide described above within the aforementioned range of the molar ratio of each component relative to the water-soluble ethylenically unsaturated monomer on the basis of the amount of the water-soluble ethylenically unsaturated monomer to be added in the reverse phase suspension polymerization in each step of the second step and later steps.

For the reaction temperature for a polymerization reaction, it is preferably 20 to 110° C., more preferably 40 to 90° C. from the viewpoint that profitability may be improved by allowing rapid progress of a polymerization to reduce a polymerization time, and polymerization heat may be easily removed to perform a smooth reaction. Further, the reaction time is preferably 0.5 to 4 hours.

<Post-Crosslinking Step>

Next, the water-absorbent resin according to the present invention can be obtained by performing post-crosslinking (post-crosslinking reaction) with a post-crosslinking agent on a hydrous gel-like material having an internal-crosslinking structure obtained by polymerizing a water-soluble ethylenically unsaturated monomer. The post-crosslinking reaction is preferably performed in the presence of the post-crosslinking agent after the polymerization of the water-soluble ethylenically unsaturated monomer. As described above, after the polymerization, the post-crosslinking reaction is performed on the hydrous gel-like material having an internal-crosslinking structure, and thus it is possible to obtain the water-absorbent resin in which the crosslinking density in the vicinity of the surface of the water-absorbent resin is increased, and various performances such as the water-absorption capacity under a load and the elasticity of the gel are enhanced.

Post-crosslinking agents can include, but are not limited to, those compounds having two or more reactive functional groups. They include, for example, polyols such as ethylene glycol, propylene glycol, 1,4-butanediol, trimethylolpropane, glycerin, polyoxyethylene glycol, polyoxypropylene glycol, and polyglycerin; polyglycidyl compounds such as (poly)ethylene glycol diglycidyl ether, (poly)glycerin diglycidyl ether, (poly)glycerin triglycidyl ether, trimethylolpropane triglycidyl ether, (poly)propylene glycol polyglycidyl ether, and (poly)glycerol polyglycidyl ether; haloepoxy compounds such as epichlorohydrin, epibromhydrin, and α-methyl epichlorohydrin; isocyanate compounds such as 2,4-tolylene diisocyanate, and hexamethylene diisocyanate; oxetane compounds such as 3-methyl-3-oxetane methanol, 3-ethyl-3-oxetane methanol, 3-butyl-3-oxetane methanol, 3-methyl-3-oxetane ethanol, 3-ethyl-3-oxetane ethanol, and 3-butyl-3-oxetane ethanol; oxazoline compounds such as 1,2-ethylenebisoxazoline; carbonate compounds such as ethylene carbonate; and hydroxyalkylamide compounds such as bis[N,N-di(β-hydroxyethyl)]adipamide. Among these post-crosslinking agents, further preferred are polyglycidyl compounds such as (poly)ethylene glycol diglycidyl ether, (poly)glycerin diglycidyl ether, (poly)glycerin triglycidyl ether, trimethylolpropane triglycidyl ether, (poly)propylene glycol polyglycidyl ether, (poly)glycerol polyglycidyl ether. These post-crosslinking agents may be used alone or in a combination of two or more.

The used amount of a post-crosslinking agent is preferably 0.00001 to 0.01 mol relative to 1 mol of the total amount of a water-soluble ethylenically unsaturated monomer used for polymerization, more preferably 0.00005 to 0.005 mol and further preferably 0.0001 to 0.002 mol.

As a method of adding a post-crosslinking agent, the post-crosslinking agent may be added as it is or as an aqueous solution. A post-crosslinking agent may also be added as a solution in which a hydrophilic organic solvent is used as a solvent, if desired. Hydrophilic organic solvents include, for example, lower alcohols such as methyl alcohol, ethyl alcohol, n-propyl alcohol, and isopropyl alcohol; ketones such as acetone, and methyl ethyl ketone; ethers such as diethyl ether, dioxane, and tetrahydrofuran; amides such as N,N-dimethylformamide; and sulfoxides such as dimethyl sulfoxide. These hydrophilic organic solvents may be used alone, in a combination of two or more, or in admixture with the water.

As for the timing when a post-crosslinking agent is added, it can be added as long as the polymerization reaction of water-soluble ethylenically unsaturated monomers has been almost completed, but it is preferably added in the presence of water in the range of 1 to 400 parts by mass relative to 100 parts by mass of a water-soluble ethylenically unsaturated monomer, more preferably added in the presence of water in the range of 5 to 200 parts by mass, further preferably added in the presence of water in the range of 10 to 100 parts by mass and further more preferably added in the presence of water in the range of 20 to 60 parts by mass. In this way, it is possible to enhance the water-absorption capacity under a load and the like. Note that the amount of water means the total amount of a water content in a reaction system and a water content used if desired when adding a post-crosslinking agent.

For the reaction temperature in the post-crosslinking reaction, it is preferably 50 to 250° C., more preferably 60 to 180° C., further preferably 60 to 140° C. and particularly preferably 70 to 120° C. Further, the reaction time of the post-crosslinking reaction is preferably set to 1 to 300 minutes, and is more preferably set to 5 to 200 minutes.

<Drying Step>

A drying step of removing water, a hydrocarbon dispersion medium and the like using distillation by applying energy such as heat from the outside after performing the aforementioned reversed phase suspension polymerization may be included. When performing dehydration of a hydrous gel after reversed phase suspension polymerization, a system in which the hydrous gel is dispersed in a hydrocarbon dispersion medium is heated to temporarily evaporate water and the hydrocarbon dispersion medium from the system by azeotropic distillation. At this time, only the evaporated hydrocarbon dispersion medium is allowed to return into the system, enabling continuous azeotropic distillation. In that case, the temperature in the system during the drying treatment is maintained at or below the azeotropic temperature of the hydrocarbon dispersion medium. Therefore this is preferred from the view point that, for example, the resin is less susceptible to deterioration. Subsequently, water and the hydrocarbon dispersion medium are evaporated away to obtain particles of a water-absorbent resin. By controlling processing conditions in this drying step after polymerization to adjust the amount of dehydrated water, the centrifugal retention rate and the like of the resulting water-absorbent resin can be controlled.

In the drying step, the drying treatment may be performed by distillation under ordinary pressure or under reduced pressure. Further, the drying treatment may be performed under a gas flow of nitrogen and the like in view of increased drying efficiency. When performing the drying treatment under ordinary pressure, a drying temperature is preferably 70 to 250° C., more preferably 80 to 180° C., further preferably 80 to 140° C. and further more preferably 90 to 130° C. Further, when performing the drying treatment under reduced pressure, a drying temperature is preferably 40 to 160° C., more preferably 50 to 110° C.

Note that in a case where post-crosslinking step is performed with a post-crosslinking agent after monomers are polymerized by reversed phase suspension polymerization, the drying step is performed by distillation as described above after the completion of the post-crosslinking step. Alternatively, the post-crosslinking step and the drying step may be performed simultaneously.

Further, if desired, various additives such as chelating agents, reducing agents, oxidizing agents, antibacterial agents, and deodorizing agents may be added to a water-absorbent resin after polymerization step, and during or after drying step.

3. Absorbent Material and Absorbent Article

The water-absorbent resin according to the present invention forms the absorbent material used for hygienic materials such as disposable diapers, sanitary napkins and incontinence pads, and is preferably used for an absorbent article including the absorbent material.

Here, an absorbent material in which a water-absorbent resin is used comprises, for example, the water-absorbent resin and a hydrophilic fiber. The structures of the absorbent material include a dispersion mixture obtained by mixing a water-absorbent resin and a hydrophilic fiber to give a uniform composition, a sandwich structure in which a water-absorbent resin is sandwiched between layered hydrophilic fibers, a structure in which a water-absorbent resin and a hydrophilic fiber are wrapped in tissue, and the like. Note that other components, for example, an adhesive binder such as thermal adhesive synthetic fibers, hot melt adhesives, and adhesive emulsions for increasing the shape retention capability of an absorbent material may be included in the absorbent material.

For the content of a water-absorbent resin in an absorbent material, it is preferably 5 to 95 mass %, more preferably 20 to 90 mass % and further preferably 30 to 80 mass %. When the content of a water-absorbent resin is less than 5 mass %, the absorption capacity of an absorbent material may be decreased, resulting in leakage and re-wet of a liquid. On the other hand, when the content of a water-absorbent resin is more than 95 mass %, the cost of an absorbent material increases, and the touch of the absorbent material becomes harder.

Hydrophilic fibers include cellulose fibers prepared from wood such as cotton-like pulp, mechanical pulp, chemical pulp, and semi-chemical pulp; artificial cellulose fibers such as rayon, and acetate; and fibers comprising synthetic resin such as hydrophilized polyamide, polyester, and polyolefine.

Moreover, an absorbent material in which a water-absorbent resin is used can be held between a liquid permeable sheet (top sheet) through which a liquid can permeate and a liquid impermeable sheet (back sheet) through which a liquid cannot permeate to give an absorbent article. The liquid permeable sheet is arranged on the side to be in contact with the body while the liquid impermeable sheet is arranged opposite to the side to be in contact with the body.

Liquid permeable sheets include nonwoven of an air through type, a span bond type, a chemical bond type, a needle punch type and the like comprising fiber such as polyethylene, polypropylene, polyester, etc. and porous synthetic resin sheets and the like. Further, liquid impermeable sheets include synthetic resin films comprising a resin such as polyethylene, polypropylene, polyvinyl chloride and the like.

EXAMPLES

4. Example

Hereafter, the present invention will be described in more detail with reference to Examples and Comparative Examples. However, the present invention shall not in any way be limited to the following Examples and the like.

4-1. Method for Evaluation Test

[Evaluation Test for Water-Absorbent Resin]

Water-absorbent resins obtained from Examples 1 to 4 below, and Comparative Examples 1 to 3 below were subjected to various tests described below for evaluation.

(1) Centrifuge Retention Rate 500 g of 0.9 mass % sodium chloride aqueous solution (physiological saline) was weighed and taken into a 500 mL beaker, and 2.0 g of a water-absorbent resin was dispersed so as not to produce lumps while being stirred at 600 r/min. The solution was left for 60 minutes while being stirred such that the water-absorbent resin was sufficiently swollen. Thereafter, the solution was poured into a cotton bag (cotton broadcloth No. 60, horizontally 100 mm×vertically 200 mm), an upper portion of the cotton bag was tied up with a rubber band, the cotton bag was dehydrated for one minute with a dehydrator (product number: H-122, manufactured by Kokusan Centrifuge Co., Ltd.) which was set such that its centrifugal force was 167 G and the mass Wa (g) of the cotton bag including the dehydrated swollen gel was measured. The same operation was performed without addition of the water-absorbent resin, the mass Wb (g) of the empty and wet cotton bag was measured and the centrifuge retention rate was calculated with the following formula.

centrifuge retention rate $(g/g) = [Wa - Wb](g)/\text{mass (g)}$ of water-absorbent resin (2) Water-Absorption Capacity of Physiological Saline Under a Load of 4.14 kPa A water-absorption capacity of physiological saline under a load of 4.14 kPa of a water-absorbent resin was measured using a measurement apparatus X. A schematic arrangement of the measurement apparatus X is shown in FIG. 1.

The measurement apparatus X shown in FIG. 1 comprises a buret part 1, a conduit 2, a measurement stage 3, and a measurement part 4 placed on the measurement stage 3. In the buret part 1, a rubber stopper 14 is connected to the upper part of a buret 10, and an air introducing pipe 11 and a cock 12 is connected to the lower part of the buret 10. Further, a cock 13 is attached to the upper part of the air introducing pipe 11. A conduit 2 connects the buret part 1 and the measurement stage 3. The diameter of the conduit 2 is 6 mm. The measurement stage 3 has a hole with a diameter of 2 mm at the center, to which the conduit 2 is connected. The measurement part 4 is provided with a cylinder 40 and a nylon mesh 41 patched on the bottom of the cylinder 40, as well as a weight 42. The inner diameter of the cylinder 40 is 2.0 cm. The nylon mesh 41 is formed as 200 mesh (75 μm openings). Further, it is configured such that a predetermined amount of a water-absorbent resin 5 is uniformly distributed on the nylon mesh 41. The weight 42 has a diameter of 1.9 cm and a mass of 119.6 g. The weight 42 is to be placed on the water-absorbent resin 5 to uniformly apply a load of 4.14 kPa to the water-absorbent resin 5.

Using the measurement apparatus X having a structure as described above, first, the cock 12 and the cock 13 at the buret part 1 were closed, and then physiological saline adjusted to 25° C. was introduced into the buret 10 from the top. Subsequently, the top of the buret was plugged with the rubber stopper 14, and then the cock 12 and the cock 13 at the buret part 1 were opened. Next, the height of the measurement stage 3 was adjusted so that the tip of the conduit 2 at the center of the measurement stage 3 was leveled with the air inlet of the air introducing pipe 11.

Meanwhile, 0.10 g of the water-absorbent resin 5 was uniformly distributed on the nylon mesh 41 in the cylinder 40, and then the weight 42 was placed on that water-absorbent resin 5. The measurement part 4 was arranged so that its center coincided with the conduit inlet at the center of the measurement stage 3.

The amount of reduced physiological saline in the buret 10 (the amount of physiological saline absorbed by the water-absorbent resin 5) Wc (mL) was continuously measured from the time point when the water-absorbent resin 5 started to absorb water. At an elapsed time of 60 minutes from the start of water absorption, a water-absorption capacity of physiological saline under a load of 4.14 kPa of the water-absorbent resin was calculated by the following formula.

water-absorption capacity of physiological saline under a load of 4.14 kPa $(mL/g) = Wc/0.10$ (g)

(3) Storage Elastic Modulus, Loss Elastic Modulus and Tan δ

As a water-absorbent resin to be measured, a water-absorbent resin was prepared so as to be passed through a sieve of 400 μm openings and to be held on a sieve of 300 μm openings, and its sized sample was swollen with physiological saline to 50 times, with the result that the 50-times swollen gel was produced. Specifically, first, 49.0 g of physiological saline was weighed and taken into a 100 mL beaker, a magnetic stirrer bar (8 mm ϕ×30 mm without a ring) was put thereinto and was arranged on a magnetic stirrer (manufactured by Iuchi Co., Ltd, HS-30D) and the magnetic stirrer was adjusted so as to be rotated at 600 r/min. Then, 1.0 g of the sized sample was put into the beaker being stirred, and was continued to be stirred until rotating vortexes disappeared such that the liquid surface became horizontal, and the 50-times swollen gel was prepared. The 50-times swollen gel was moved to a centrifuge tube, was degassed for four minutes with a dehydrator (product number: H-103NA SERIES, manufactured by Kokusan Centrifuge Co., Ltd.) which was set such that its centrifugal force was 671 G and was used as a measurement sample.

In the measurement, the prepared measurement sample was set to a dynamic viscoelasticity measuring device rheometer (product number: AR2000eZ, manufactured by TA Instruments Japan Ltd.), and the frequency ω (rad/second) dispersion of a storage elastic modulus G' (Pa) and a loss elastic modulus G" (Pa) was measured. As a sample holder, a parallel plate having a diameter of 60 mm was used, and a distance between plates was set to 3 mm. The thickness of the gel was set to 3000 μm. The measurement temperature was set to 25° C., and the measurement was performed under conditions in which frequency ω=range of 0.1 to 300 rad/second and strain=0.1% strain.

Then, the storage elastic modulus G' (Pa) and the loss elastic modulus G" (Pa) at 10 rad/second were determined, and then, the value of tan δ was calculated from a ratio (G"/G') of G" to G' and its value was regarded as tan δ of the water-absorbent resin.

(4) Median Particle Diameter (Particle Size Distribution)

To 50 g of a water-absorbent resin, 0.25 g of amorphous silica (made by Evonik Degussa Japan, Inc., Carplex #80) was mixed as a lubricant. The median particle diameter thereof was measured with a combination of sieves of [A] below.

[A] JIS standard sieves were combined in the following order from the top: a sieve of 850 µm openings, a sieve of 600 µm openings, a sieve of 500 µm openings, a sieve of 400 µm openings, a sieve of 300 µm openings, a sieve of 250 µm openings, a sieve of 150 µm openings and a receiving tray.

The water-absorbent resin was introduced into the top of the combined sieves, and then shaken for 20 minutes using a low-tap shaker for classification. After classification, the mass of the water-absorbent resin which remained in each sieve was calculated as a mass proportion of particles relative to the total mass to obtain a particle size distribution. By integrating the amount on each sieve from the one having the largest particle diameter in this particle size distribution, the relationship between the sieve openings and the integrated value of the mass proportion of particles of the water-absorbent resin which remained in the sieves was plotted on logarithmic probability paper. By connecting the plots on the probability paper with a straight line, a particle diameter corresponding to 50 mass % in the integrated mass proportion of particles was taken as the median particle diameter.

Note that the mass proportion of particles from 300 to 400 µm particles in the total water-absorbent resin is a mass proportion of particles from a water-absorbent resin which remained in the sieve with 300 µm openings relative to the whole proportion in the aforementioned measurements. Similarly, the mass proportion of particles from 150 to 850 µm particles in the total water-absorbent resin is a value obtained by summing the mass proportion of particles of the water-absorbent resin which remained in sieves with openings of 150 µm, 250 µm, 300 µm, 400 µm, 500 µm, 600 µm.

[Evaluation Test of Absorbent Material in which Water-Absorbent Resin is Used and Absorbent Article]

(1) Production of Absorbent Material and Absorbent Article 12 g of the water-absorbent resin and 12 g of crushed pulp (made by Rayonier, Rayfloc) were used and were uniformly mixed by air papermaking, and thus an absorbent material core in the shape of a sheet of 40 cm×12 cm was produced. Next, while the absorbent material core was placed between two tissue papers, each of which had the same size as the absorbent material core and a basis weight of 16 g/m2, the absorbent material core was all over pressed with a load of 196 kPa for 30 seconds to prepare an absorber absorbent material. Furthermore, on the upper surface of the absorbent material, a polyethylene-polypropylene air-through type porous liquid permeable sheet having the same size as the absorbent material and a basis weight of 22 g/m$^2$ was arranged, and a polyethylene liquid impermeable sheet having the same size and the same basis weight was arranged on the lower surface of the absorbent material and the absorbent material was sandwiched therebetween to form an absorbent article (size: 40×12 cm).

(2) Preparation of Artificial Urine

As artificial urine, 0.780 mass % of NaCl, 0.022 mass % of $CaCl_2$ and 0.038 mass % of $MgSO_4$ were mixed and dissolved with ion exchange water, a small amount of blue No. 1 was mixed and thus artificial urine was prepared.

(3) Permeation Rate

The absorbent article was placed on a horizontal stage. On the center portion of the absorbent article, a measuring instrument that had a liquid injection cylinder having an inner diameter of 3 cm on the center of a plate whose bottom surface was 10 cm×10 cm and that had a mass of 2 kg was placed, and thus a load was placed on the absorbent article. Then, 80 mL of artificial urine was injected into the cylinder at a time and the time elapsed until the artificial urine completely disappeared from the cylinder was measured using a stopwatch, and was set to the first permeation rate (second). Then, the cylinder was removed, the absorbent article was stored as it was, the same operation was performed with the measuring instrument used in the same position as in the first measurement both 30 minutes and 60 minutes after the start of the first injection of the artificial urine and the second and third permeation rates (second) were measured. The total of the first to third permeation rates was assumed to be the total permeation rate. It can be said that as the permeation rate is shorter, the absorbent article is more preferable.

(4) Amount of Re-Wet

At 120 minutes after the start of the first injection of the artificial urine in the measurement of the permeation rate described above, in the vicinity of the position of the injection of the artificial urine on the absorbent article, filter paper 10 cm square whose mass (Wd (g), about 50 g) was previously measured was placed and a weight having a bottom surface of 10 cm×10 cm and a mass of 5 kg was placed thereon. After the loading for five minutes, the mass (We (g)) of the filter paper was measured, and the increased mass was assumed to be the amount (g) of re-wet. It can be said that as the amount of re-wet is lower, the absorbent article is more preferable.

Amount of re-wet (g)=We−Wd 4-2. Examples and Comparative Example

Example 1

A 2 L cylindrical round-bottom separable flask with an inner diameter of 110 mm was prepared and equipped with a reflux condenser, a dropping funnel, a nitrogen gas-introducing tube and stirrer having stirring blades compound of two sets of 4 inclined paddle blades with a blade diameter of 50 mm. To this flask, 300 g of n-heptane was introduced as a hydrocarbon dispersion medium, 0.74 g of sucrose stearic acid ester of HLB3 (made by Mitsubishi-Kagaku Foods Corporation, RYOTO sugar ester S-370) was added as a surfactant and 0.74 g of maleic anhydride modified ethylene-propylene copolymer (made by Mitsui Chemicals, Inc., High Wax 1105A) was added as a polymeric dispersion agent, and heated to 80° C. with stirring, and a surfactant was dissolved, and then cooled to 50° C.

Meanwhile, 92 g (1.02 mol) of 80 mass % aqueous solution of acrylic acid was introduced into a 500 mL Erlenmeyer flask, and 102.2 g of 30 mass % aqueous solution of sodium hydroxide was added dropwise while cooling from the outside to perform 75 mol % neutralization. Subsequently, 0.092 g of hydroxyethyl cellulose (made by Sumitomo Seika Chemicals Co., Ltd., HEC AW-15F) as a thickener, 0.092 g (0.339 mmol) of 2,2'-azobis(2-amidino-propane)dihydrochloride as an azo based compound, 0.037 g (0.137 mmol) of potassium persulfate as a peroxide, 0.010 g (0.058 mmol) of ethylene glycol diglycidyl ether as an internal-crosslinking agent and 43.8 g of ion exchange water were added and dissolved to prepare a first-step aqueous monomer solution.

Then, the aqueous monomer solution prepared as described above was added to a separable flask, and the atmosphere in the system was thoroughly replaced with nitrogen. Then, the flask was immersed into a 70° C. water bath to raise temperature, and a first-step polymerization was performed for 60 minutes to obtain a first-step polymerized slurry.

Meanwhile, 128.8 g (1.43 mol) of 80 mass % aqueous solution of acrylic acid was introduced to another 500 mL Erlenmeyer flask, and 143.1 g of 30 mass % aqueous solution of sodium hydroxide was added dropwise while cooling from the outside to perform 75 mol % neutralization. Then, 0.129 g (0.475 mmol) of 2,2'-azobis(2-amidinopropane)dihydrochloride as an azo based compound, 0.052 g (0.191 mmol) of potassium persulfate as a peroxide, 0.012 g (0.067 mmol) of ethylene glycol diglycidyl ether as an internal-crosslinking agent and 15.9 g of ion exchange water were added and dissolved to prepare a second-step aqueous monomer solution.

After cooling the system in the aforementioned separable flask to 25° C., all of the second-step aqueous monomer solution was added to the first-step polymerized slurry, and the atmosphere in the system was thoroughly replaced with nitrogen. Subsequently, the flask was again immersed into a 70° C. water bath to raise temperature, and a second-step polymerization was performed for 30 minutes.

After the second-step polymerization, the reaction liquid was heated to 125° C. in an oil bath, and 236 g of water was removed from the system by refluxing n-heptane in azeotropic distillation of n-heptane and water. Then, 4.42 g (0.51 mmol) of 2 mass % aqueous solution of ethylene glycol diglycidyl ether was added as a post-crosslinking agent, and maintained at 80° C. for 2 hours. Subsequently, drying step was performed by evaporating n-heptane, and then a dried resin was obtained. The dried resin was allowed to pass through a sieve with 1000 μm openings to obtain 234.1 g of a water-absorbent resin in a form of agglomerated spherical particles. The water-absorbent resin obtained in this way was evaluated in accordance with the various test methods as described above.

Note that for the water-absorbent resin obtained, the mass proportion of particles from 150 to 850 μm relative to the whole proportion was 94 mass % and the mass proportion of particles from 300 to 400 μm relative to the whole proportion was 36 mass %.

Example 2

Example 2 was the same as Example 1 except that after the second-step polymerization, 239 g of water was removed from the system by refluxing n-heptane in azeotropic distillation of n-heptane and water. Thereby, 231.2 g of a water-absorbent resin that differs from the water-absorbent resin obtained in Example 1 in the centrifugal retention rate and the like. The water-absorbent resin thus obtained was evaluated according to the various types of test methods described above.

Note that for the water-absorbent resin obtained, the mass proportion of particles from 150 to 850 μm relative to the whole proportion was 92 mass % and the mass proportion of particles from 300 to 400 μm relative to the whole proportion was 32 mass %.

Example 3

Example 3 was the same as Example 1 except that as an internal-crosslinking agent which was dissolved in a first-step monomer aqueous solution, 0.020 g (0.116 mmol) of ethylene glycol diglycidyl ether was used and that after the second-step polymerization, 254 g of water was removed from the system by refluxing n-heptane in azeotropic distillation of n-heptane and water. Thereby, 232.9 g of a water-absorbent resin that differs from the water-absorbent resin obtained in Example 1 in the amount of internal-crosslinking agent. The water-absorbent resin thus obtained was evaluated according to the various types of test methods described above.

Note that for the water-absorbent resin obtained, the mass proportion of particles from 150 to 850 μm relative to the whole proportion was 95 mass % and the mass proportion of particles from 300 to 400 μm relative to the whole proportion was 33 mass %.

Example 4

Example 4 was the same as Example 3 except that after the second-step polymerization, 258 g of water was removed from the system by refluxing n-heptane in azeotropic distillation of n-heptane and water. Thereby, 226.0 g of a water-absorbent resin that differs from the water-absorbent resin obtained in Example 1 in the centrifugal retention rate and the like. The water-absorbent resin thus obtained was evaluated according to the various types of test methods described above.

Note that for the water-absorbent resin obtained, the mass proportion of particles from 150 to 850 μm relative to the whole proportion was 95 mass % and the mass proportion of particles from 300 to 400 μm relative to the whole proportion was 33 mass %.

Comparative Example 1

In Comparative Example 1, a 2 L cylindrical round-bottom separable flask with an inner diameter of 110 mm was prepared and equipped with a reflux condenser, a dropping funnel, a nitrogen gas-introducing tube and stirrer having stirring blades compound of two sets of 4 inclined paddle blades with a blade diameter of 50 mm. To this flask, 300 g of n-heptane was introduced as a hydrocarbon dispersion medium, 0.74 g of sucrose stearic acid ester of HLB3 (made by Mitsubishi-Kagaku Foods Corporation, Ryoto sugar ester S-370) was added as a surfactant and 0.74 g of maleic anhydride modified ethylene-propylene copolymer (made by Mitsui Chemicals, Inc., High Wax 1105A) was added as a polymeric dispersion agent, and heated to 80° C. with stirring, and a surfactant was dissolved, and then cooled to 50° C.

Meanwhile, 92 g (1.02 mol) of 80 mass % aqueous solution of acrylic acid was introduced into a 500 mL Erlenmeyer flask, and 102.2 g of 30 mass % aqueous solution of sodium hydroxide was added dropwise while cooling from the outside to perform 75 mol % neutralization. Subsequently, 0.092 g of hydroxylethyl cellulose (made by Sumitomo Seika Chemicals Co., Ltd., HEC AW-15F) as a thickener, 0.074 g (0.274 mmol) of potassium persulfate as a peroxide, 0.010 g (0.058 mmol) of ethylene glycol diglycidyl ether as an internal-crosslinking agent and 43.8 g of ion exchange water were added and dissolved to prepare an aqueous monomer solution.

Then, the aqueous monomer solution prepared as described above was added to a separable flask, and the atmosphere in the system was thoroughly replaced with nitrogen. Then, the flask was immersed into a 70° C. water bath to raise temperature, and a first-step polymerization was performed for 60 minutes to obtain a first-step polymerized slurry.

Meanwhile, 128.8 g (1.43 mol) of 80 mass % aqueous solution of acrylic acid was introduced to another 500 mL Erlenmeyer flask, and 143.1 g of 30 mass % aqueous solution of sodium hydroxide was added dropwise while cooling from the outside to perform 75 mol % neutralization. Then, 0.104 g (0.382 mmol) of potassium persulfate as a peroxide, 0.012 g (0.067 mmol) of ethylene glycol diglycidyl ether as an internal-crosslinking agent and 15.9 g were added and dissolved to prepare a second-step aqueous monomer solution.

After cooling the system in the aforementioned separable flask to 25° C., all of the second-step aqueous monomer solution was added to the first-step polymerized slurry, and the atmosphere in the system was thoroughly replaced with nitrogen. Subsequently, the flask was again immersed into a 70° C. water bath to raise temperature, and a second-step polymerization was performed for 30 minutes.

After the second-step polymerization, the reaction liquid was heated to 125° C. in an oil bath, and 257 g of water was removed from the system by refluxing n-heptane in azeotropic distillation of n-heptane and water. Then, 4.42 g (0.51 mmol) of 2 mass % aqueous solution of ethylene glycol diglycidyl ether was added as a post-crosslinking agent, and maintained at 80° C. for 2 hours. Subsequently, drying step was performed by evaporating n-heptane to obtain a dried resin. The dried resin was allowed to pass through a sieve with 1000 μm openings to obtain 228.2 g of a water-absorbent resin in a form of agglomerated spherical particles. The water-absorbent resin obtained in this way was evaluated in accordance with the various test methods as described above. Note that for the water-absorbent resin obtained, the mass proportion of particles from 150 to 850 μm relative to the whole proportion was 94 mass % and the mass proportion of particles from 300 to 400 μm relative to the whole proportion was 33 mass %.

Comparative Example 2

Comparative Example 2 was the same as Comparative Example 1 except that after the second-step polymerization, 259 g of water was removed from the system by refluxing n-heptane in azeotropic distillation of n-heptane and water. Thereby, 228.2 g of a water-absorbent resin that differs from the water-absorbent resin obtained in Comparative Example 1 in the centrifugal retention rate and the like. The water-absorbent resin thus obtained was evaluated according to the various types of test methods described above.

Note that for the water-absorbent resin obtained, the mass proportion of particles from 150 to 850 μm relative to the whole proportion was 94 mass % and the mass proportion of particles from 300 to 400 μm relative to the whole proportion was 31 mass %.

Comparative Example 3

In Comparative Example 3, as compared with the water-absorbent resin obtained in Comparative Example 1, a water-absorbent resin to which a large amount of crosslinking agent was added was obtained.

Specifically, first, a 2 L cylindrical round-bottom separable flask with an inner diameter of 110 mm was prepared and equipped with a reflux condenser, a dropping funnel, a nitrogen gas-introducing tube and stirrer having stirring blades compound of two sets of 4 inclined paddle blades with a blade diameter of 50 mm. To this flask, 300 g of n-heptane was introduced as a hydrocarbon dispersion medium, 0.74 g of sucrose stearic acid ester of HLB3 (made by Mitsubishi-Kagaku Foods Corporation, Ryoto sugar ester S-370) was added as a surfactant and 0.74 g of maleic anhydride modified ethylene-propylene copolymer (made by Mitsui Chemicals, Inc., High Wax 1105A) was added as a polymeric dispersion agent, and heated to 80° C. with stirring, and a surfactant was dissolved, and then cooled to 50° C.

Meanwhile, 92 g (1.02 mol) of 80 mass % aqueous solution of acrylic acid was introduced into a 500 mL Erlenmeyer flask, and 102.2 g of 30 mass % aqueous solution of sodium hydroxide was added dropwise while cooling from the outside to perform 75 mol % neutralization. Subsequently, 0.092 g of hydroxyethyl cellulose (made by Sumitomo Seika Chemicals Co., Ltd., HEC AW-15F) as a thickener, 0.074 g (0.274 mmol) of potassium persulfate as a peroxide, 0.018 g (0.106 mmol) of ethylene glycol diglycidyl ether as an internal-crosslinking agent and 43.8 g were added and dissolved to prepare an aqueous monomer solution.

Then, the aqueous monomer solution prepared as described above was added to a separable flask, and the atmosphere in the system was thoroughly replaced with nitrogen. Then, the flask was immersed into a 70° C. water bath to raise temperature, and a first-step polymerization was performed for 60 minutes to obtain a first-step polymerized slurry.

Meanwhile, 128.8 g (1.43 mol) of 80 mass % aqueous solution of acrylic acid was introduced to another 500 mL Erlenmeyer flask, and 143.1 g of 30 mass % aqueous solution of sodium hydroxide was added dropwise while cooling from the outside to perform 75 mol % neutralization. Then, 0.104 g (0.382 mmol) of potassium persulfate as a peroxide, 0.039 g (0.222 mmol) of ethylene glycol diglycidyl ether as an internal-crosslinking agent and 15.9 g of ion exchange water were added and dissolved to prepare a second-step aqueous monomer solution.

After cooling the system in the aforementioned separable flask to 25° C., all of the second-step aqueous monomer solution was added to the first-step polymerized slurry, and the atmosphere in the system was thoroughly replaced with nitrogen. Subsequently, the flask was again immersed into a 70° C. water bath to raise temperature, and a second-step polymerization was performed for 30 minutes.

After the second-step polymerization, the reaction liquid was heated to 125° C. in an oil bath, and 273 g of water was removed from the system by refluxing n-heptane in azeotropic distillation of n-heptane and water. Then, 6.63 g (0.761 mmol) of 2 mass % aqueous solution of ethylene glycol diglycidyl ether was added as a post-crosslinking agent, and maintained at 80° C. for 2 hours. Subsequently, drying step was performed by evaporating n-heptane to obtain a dried resin. The dried resin was allowed to pass through a sieve with 1000 μm openings to obtain 231.2 g of a water-absorbent resin in a form of agglomerated spherical particles. The water-absorbent resin obtained in this way was evaluated in accordance with the various test methods as described above. Note that for the water-absorbent resin obtained, the mass proportion of particles from 150 to 850 μm relative to the whole proportion was 94 mass % and the mass proportion of particles from 300 to 400 μm relative to the whole proportion was 39 mass %.

4-3. Evaluation Results

[Evaluation of Water-Absorbent Resin]

The evaluation results of the water-absorbent resins are shown in table 1 below. In table 1, absorption capacity elasticity indexes represented by formula (I) below are also shown.

$$\text{absorption capacity elasticity index} = \text{storage elastic modulus [Pa]} \times \text{centrifugal retention rate [g/g]} \quad (I)$$

TABLE 1

|  | Centrifugal retention rate (g/g) | Storage elastic modulus (Pa) | Loss elastic modulus (Pa) | tan δ (×10$^{-2}$) | Absorption capacity elasticity index | Water-absorption capacity of physiological saline under a load of 4.14 kPa (ml/g) | Median particle diameter (μm) |
|---|---|---|---|---|---|---|---|
| Example 1 | 42 | 1760 | 25 | 1.45 | 73920 | 24 | 335 |
| Example 2 | 48 | 1550 | 23 | 1.48 | 74400 | 18 | 340 |
| Example 3 | 41 | 1940 | 28 | 1.43 | 79540 | 22 | 370 |
| Example 4 | 49 | 1690 | 28 | 1.67 | 82810 | 18 | 375 |
| Comparative Example 1 | 40 | 1620 | 35 | 2.15 | 64800 | 15 | 365 |
| Comparative Example 2 | 46 | 1410 | 36 | 2.55 | 64860 | 13 | 370 |
| Comparative Example 3 | 31 | 2130 | 43 | 2.02 | 66030 | 26 | 360 |

As is understood from the results shown in table 1, the water-absorbent resins obtained in Examples 1 to 4 were water-absorbent resins which had the intended performance.

[Evaluation Results of Absorbent Articles]

Then, in table 2 below, on the absorbent articles produced by using the water-absorbent resins obtained in Examples 1 to 3 and Comparative Examples 1 and 3 described above, the results of the measurements of the permeation rate of the artificial urine, the amount of re-wet and the diffusion length are shown.

TABLE 2

|  | Storage elastic modulus (Pa) | Centrifugal retention rate (g/g) | Absorption capacity elasticity index | Performance evaluation of absorbent article | | | | | |
|---|---|---|---|---|---|---|---|---|---|
|  |  |  |  | Permeation rate (Second) | | | | Amount of re-wet (g) | Diffusion length (cm) |
|  |  |  |  | First time | Second time | Third time | Total |  |  |
| Example 1 | 1760 | 42 | 73920 | 63 | 94 | 107 | 265 | 1.3 | 25 |
| Example 2 | 1550 | 48 | 74400 | 64 | 103 | 121 | 288 | 0.4 | 25 |
| Example 3 | 1940 | 41 | 79540 | 58 | 83 | 102 | 242 | 1.0 | 26 |
| Comparative Example 1 | 1620 | 40 | 64800 | 63 | 143 | 171 | 377 | 8.0 | 23 |
| Comparative Example 3 | 2130 | 31 | 66030 | 62 | 99 | 129 | 290 | 7.4 | 24 |

As shown in the results of table 2, it is demonstrated that the absorbent articles using the water-absorbent resins which were obtained in Examples 1 to 3 and whose absorption capacity elasticity indexes were 68000 or more are better in the permeation rate and the amount of re-wet that are the absorption performance under a load as compared with the absorbent articles produced by using the water-absorbent resins obtained in Comparative Examples.

EXPLANATION OF REFERENCE NUMERALS

X measurement apparatus
1 buret part
2 conduit
3 measurement stage
4 measurement part
5 water-absorbent resin

The invention claimed is:

1. A water-absorbent resin which is obtained by polymerizing a water-soluble ethylenically unsaturated monomer in presence of an internal-crosslinking agent and performing post-crosslinking with a post-crosslinking agent, wherein a water-absorption capacity of physiological saline under a load of 4.14 kPa is 16 mL/g or more,
a mass proportion of particles from 150 to 850 μm relative to the whole proportion is 85 mass % or more, moreover a mass proportion of particles from 300 to 400 μm relative to the whole proportion is 20 mass % or more,
an absorption capacity elasticity index represented by formula (I) is 68000 or more, and
the absorption capacity elasticity index=storage elastic modulus [Pa]×centrifugal retention rate [g/g] . . . (I).

2. The water-absorbent resin according to claim 1, wherein tan δ measured by sizing the 300 to 400 μm particles of the water-absorbent resin is 2.00×10$^{-2}$ or less.

3. An absorbent article which is formed with an absorbent material containing the water-absorbent resin according to claim 1.

4. An absorbent article which is formed with an absorbent material containing the water-absorbent resin according to claim 2.

5. The water-absorbent resin according to claim 1, wherein the polymerizing a water-soluble ethylenically unsaturated monomer in presence of an internal-crosslinking agent, is performed in presence of an azo based compound and a peroxide, the azo based compound being present in a proportion of 40 mass % or more and 80 mass % or less in the total used amount of the azo based compound and the peroxide.

* * * * *